United States Patent [19]
Lang

[11] Patent Number: 5,688,244
[45] Date of Patent: Nov. 18, 1997

[54] APPARATUS FOR MONITORING INFUSION

[76] Inventor: Volker Lang, Zugspitzstrasse 52 82131, Gauting, Germany

[21] Appl. No.: 403,791
[22] PCT Filed: Mar. 30, 1994
[86] PCT No.: PCT/EP94/01004
   § 371 Date: Apr. 28, 1995
   § 102(e) Date: Apr. 28, 1995
[87] PCT Pub. No.: WO95/03079
   PCT Pub. Date: Feb. 2, 1995

[30] Foreign Application Priority Data

Jul. 20, 1993 [DE] Germany ............... 43 24 230.8
Oct. 29, 1993 [DE] Germany ............... 43 37 017.9
Nov. 29, 1993 [DE] Germany ............... 43 40 536.3

[51] Int. Cl.$^6$ ................................................. A61M 1/00
[52] U.S. Cl. ..................... 604/118; 604/65; 604/247; 128/675; 200/834; 200/83 W
[58] Field of Search ................... 604/30, 31, 50, 604/65, 66, 67, 118, 245, 246, 247, 250, 256; 128/672, 674, 675, 912; 200/83 R, 83 B, 83 J, 33 Q, 33 Y, 83 W, 83 Z

[56] References Cited

U.S. PATENT DOCUMENTS

| 3,731,679 | 5/1973 | Wilheimson et al. | |
| 4,613,325 | 9/1986 | Abrams | 604/118 |
| 4,994,035 | 2/1991 | Mokros | 604/118 |
| 5,195,986 | 3/1993 | Kamen | 604/132 |
| 5,211,201 | 5/1993 | Kamen et al. | 604/123 |

FOREIGN PATENT DOCUMENTS

| 0 018 649 | 11/1980 | European Pat. Off. |
| 3816128 | 9/1989 | Germany |
| 87 05225 | 9/1987 | WIPO |

Primary Examiner—Mark Bockelman
Assistant Examiner—Ronald K. Stright, Jr.
Attorney, Agent, or Firm—Jacobson, Price, Holman & Stern, PLLC

[57] ABSTRACT

An apparatus for infusion monitoring including a pressure transmission line branched from the infusion hose and a diaphragm connected with the infusion hose, the diaphragm being able to be connected with a pressure sensor for registering a change in curvature of the diaphragm. In order to achieve the aim of providing an apparatus of this type which renders possible on the one hand a reliable monitoring of infusion and on the other hand a way of preventing the production of a false alarm in a substantially reliable fashion, the apparatus of this type is so designed that in the infusion hose between the branch point of the pressure transmission line and the free end, adjacent to the patient, of the infusion hose a one-way valve is arranged, which permits a direction of flow to the patient.

19 Claims, 4 Drawing Sheets 5,688,244

APPARATUS FOR MONITORING INFUSION

FIELD OF THE INVENTION

The invention relates to an apparatus for monitoring infusion.

BACKGROUND OF THE INVENTION

For intravenous infusion therapy at the present time gravity feed infusion systems with peristaltic, hose, cassette and injection pumps are employed for various infusion solutions supplied to the patient, normally with the aid of a hollow needle or vein catheter. Owing to movement of the patient during such infusion therapy there may be a partial or complete arrest or stopping of infusion, which in part only lasts a few seconds, but may well last longer. Such phenomena may be due to kinking of the infusion hose adjacent to the Patient or of draining veins, displacement of the infusion needle in the vein, engagement of the catheter tip with the vein wall, partial or complete blockage by a blood clot or the like.

Partial or complete arrest of infusion naturally has to be dealt with as soon as possible. Two important examples in this respect are the vital necessity for an uninterrupted supply of medicament and the maintenance of vitally necessary venous access to the circulatory system. On the occurrence of each partial or complete infusion arrest into the vein of a patient there is at least initially an increase in the pressure in the infusion hose system owing to the continued pumping action by the infusion apparatus. This increase in pressure may be measured and by setting certain alarm limits on a monitor screen can be utilized for monitoring infusion. However in the case of infusion systems presently employed such increase in pressure unfortunately takes place very slowly owing to the comparatively large capability of expansion and in the case of low infusion rates will occur only after half an hour or even not at all. The equipment presently commercially available so far is still only able to be used technically to a limited extent.

The German patent publication 3,816,128 C1 discloses for example such a pressure warning arrangement for infusion apparatus. This apparatus more particularly suffers from the disadvantage that even a slight movement of the patient with whom the infusion system is connected will lead to a spurious alarm being raised owing to back pressure and an arrest of infusion for a short time.

SUMMARY OF THE INVENTION

One object of the invention is, taking as a starting point the prior art of the type initially mentioned, to provide an apparatus for monitoring infusions such that on the one hand there is the reliable possibility of ensuring such monitoring even at minimum infusion rates while on the other hand the raising of a spurious alarm is substantially safely prevented.

In accordance with such features between the branch point of the pressure transmission line and the free end adjacent to the patient of the infusion hose a one-way valve is arranged, which renders possible a flow direction toward the patient.

The presence of this one-way valve constitutes a certain way of preventing any back pressure, due to movements of the patient, in the infusion system leading to an alarm being raised spuriously.

BRIEF DESCRIPTION OF THE DRAWINGS

Further advantageous developments and convenient forms of the invention will be understood from the following detailed descriptive disclosure of embodiments thereof in conjunction with the accompanying drawings.

DETAILED DESCRIPTION OF THE PREFERRED EMBODIMENTS

Figure 1:
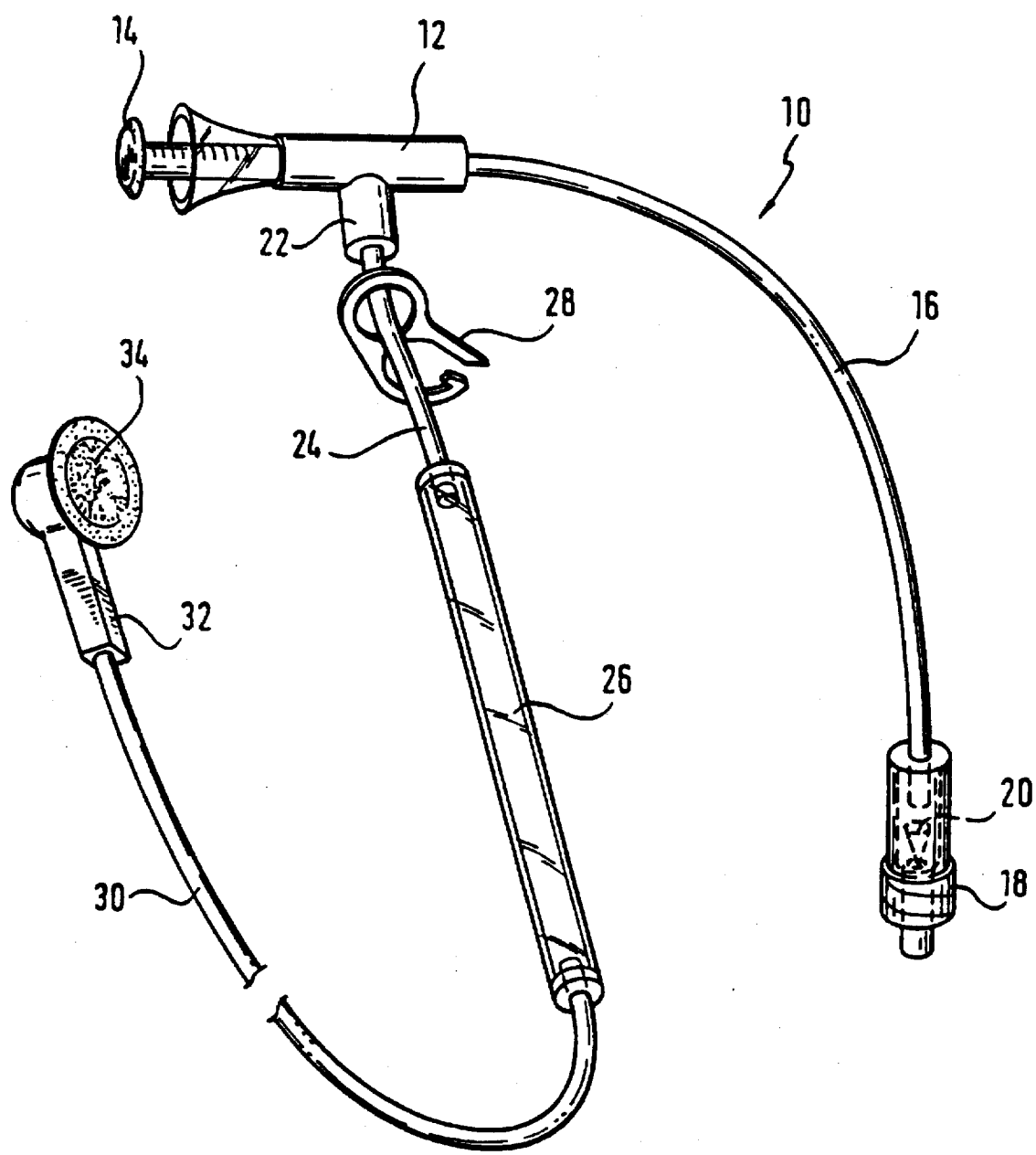
FIG. 1 shows a first embodiment or an apparatus for infusion monitoring in accordance with the present invention.

The first simple embodiment depicted in FIG. 1 comprises an apparatus for infusion monitoring 10, which may also be a sterile apparatus for use once only, for infusion monitoring adjacent to the patient. The apparatus 10 has as its main parts a T union 12, on whose left limb a female standard Luer connector 14 is arranged for the connection of an infusion device and on whose right limb a short infusion hose 16 is arranged, which ends in a special purpose male Luer connector 18 with a built-in one-way valve 20, which permits flow in the direction toward the patient. The Luer adapter 18 serves for the connection of, for example, a hollow needle (not illustrated) or of a vein catheter (not illustrated either). On the third limb 22 of the T union there is a short piece of narrow-tureen and thick-walled hose 24, which is able to be shut off upstream from the opening into an air chamber 26 by means of a hose clamp 28, which can be locked. The air chamber 26 is for example embodied in the form of a piece of short transparent and thick-walled, wide-lumen hose. From the free end of the air chamber 26 there leads a transparent, thick-walled and narrow-lumen pressure transmission hose 30 with a length of 50 to 150 cm to a pressure transmission capsule 32, which contains a welded on thin diaphragm 34. It is from this diaphragm that the infusion pressure to be measured may be transmitted in a known manner to a pressure sensitive sensor (an electronic pressure sensor capsule, a spring-loaded limit switch or the like) and after electronic signal evaluation may be employed for optical and acoustic alarm signal production.

The apparatus 10 in accordance with FIG. 1 may be employed as follows. After previously closing of the hose 24 by the clamp 28 with a built-in one-way valve 20 the apparatus 10 including the Luer connector 18 filled with infusion solution in a manner free of bubbles. Then the apparatus is connected with the venous access point to the patient (vein catheter, hollow needle). It is only after the pressure transmission cable 32 has been inserted in the electronic pressure monitoring apparatus, as in accordance with the prior art, that the hose clamp 28 is opened. Accordingly infusion liquid makes its way through a short piece of narrow-lumen, hose 24 in a manner dependent on the available infusion pressure in the large-lumen air chamber 26 to a greater or lesser extent and causes a displacement of the air, which acting via the pressure transmission hose 30 leads to a corresponding curving or bulging of the pressure transmission diaphragm 34 of the pressure capsule 32 to the electronic pressure sensor (not illustrated). The air chamber 26 is preferably of such a size that during routine infusion pressure measurements there is no access of infusion liquid to the connected narrow-lumen pressure transmission hose 30. The passage of liquid, for example at a high infusion pressure, into this hose would, in view of its narrow lumen, prevent a return flow during the following normalization of the infusion pressure owing to the capillary forces acting and accordingly lead to an undesired continuous alarm signal being produced.

Since however in the case of monitoring of the infusion pressure alone, spurious alarms may be produced in the case of even a slight movement of the patient's arm employed for infusion (owing to a brief interference or interruption in the venous flow of the infusion solution or the production of powerful pressure waves even because of a brief, sudden kinking of the infusion line or of the intravenous catheter in the patient) all these pressure increases produced from the patient side via return flows are eliminated by the inclusion of the one-way valve 20 in the system. Owing to this feature and a fixed or adjustable alarm delay of 10 to 60 seconds additionally incorporated in the electronic pressure-alarm apparatus, it is possible to ensure a very high degree of freedom from false alarms, something which frees nursing staff for other duties without this being at the sacrifice of a clinically relevant delay in raising an alarm and accordingly to a patient-related hazard.

Figure 2:
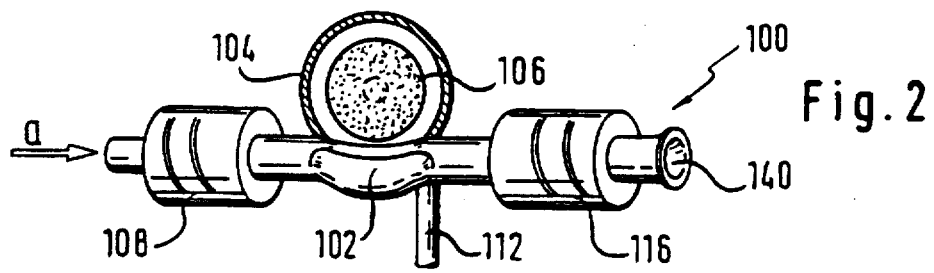
FIG. 2 is a perspective elevation of a second embodiment of an apparatus for infusion monitoring.

In FIGS. 2 through 5 a second embodiment of an apparatus 100 for infusion monitoring will be seen. Its main parts are a pressure transmission capsule 102, which as shown in FIG. 2 has a rim 104 and an inserted diaphragm 106 for pressure transmission. On one side of the pressure transmission capsule 102 there is a male standard Luer connector 108 with an integrated one-way valve 110 (see for example FIG. 3) for the connection of infusion equipment. On the opposite side of the pressure measuring capsule 102 there is the end of a hose 112 for the administration of medicaments having a Luer connector 114 (see FIG. 3). Furthermore on this side as well of the pressure transmission capsule 102 there is a female standard Luer connector 116 with an integrated one-way valve 118 (see FIG. 3). Same may be connected for example with a hollow infusion needle or a vein catheter 120 (see FIG. 5).

Figure 3:
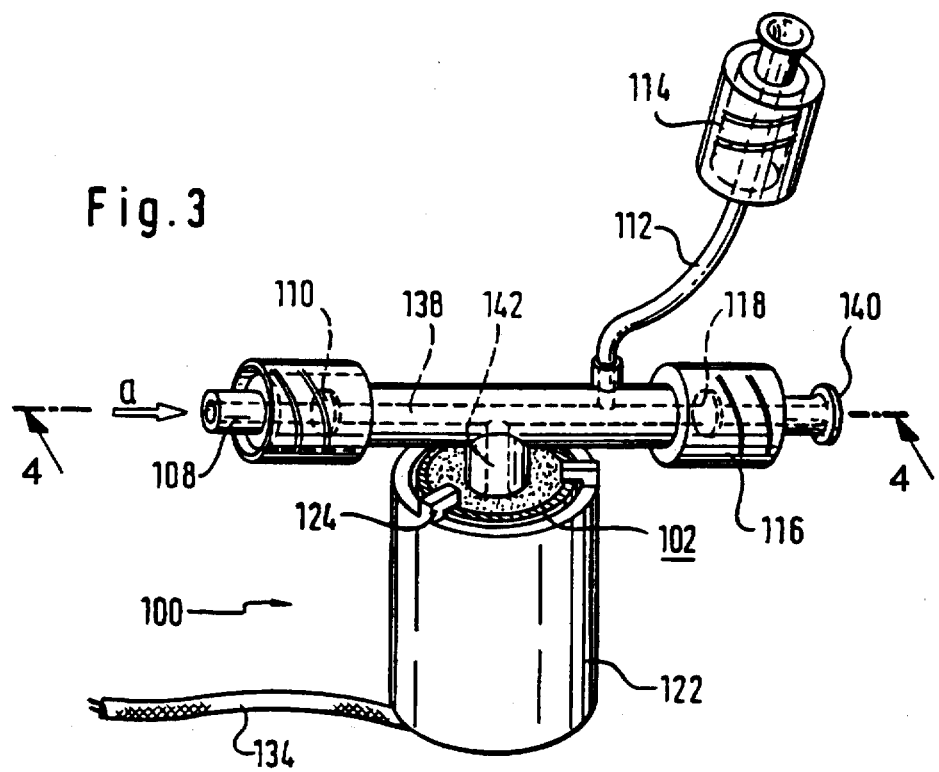
FIG. 3 is a perspective representation of the electronic pressure sensor with a protective housing and a holding device for the apparatus for infusion monitoring in accordance with the embodiment of FIG. 2.

FIG. 3 indicates how the pressure transmission capsule 102 is incorporated in a housing 122. The pressure transmission capsule 102 is, as clearly indicated in the partially sectioned representation of FIG. 3 and the section of FIG. 4, fixed in place by a holding means 124 in the form of a projecting rim of the housing 122. In the housing 122 an electronic pressure sensor 123 of conventional design is arranged having an associated diaphragm 126. The pressure sensor 123 is thrust at its rim 130 firmly against the rim 104 of the pressure transmission capsule 102 by way of a disk-like compression spring 128. Accordingly the diaphragm 126 of the pressure sensor 123 is in contact with the diaphragm 106 of the pressure transmission capsule 102. The diaphragm 126 causes the diaphragm 106 to bulge inward so that a narrow gap space 132 (see FIG. 4) is produced. The signal, detected by the electronic pressure sensor 123 and then evaluated, passes by way of the connecting cable 134 to an electronic monitor device 136 (see FIG. 5).

Figure 4:
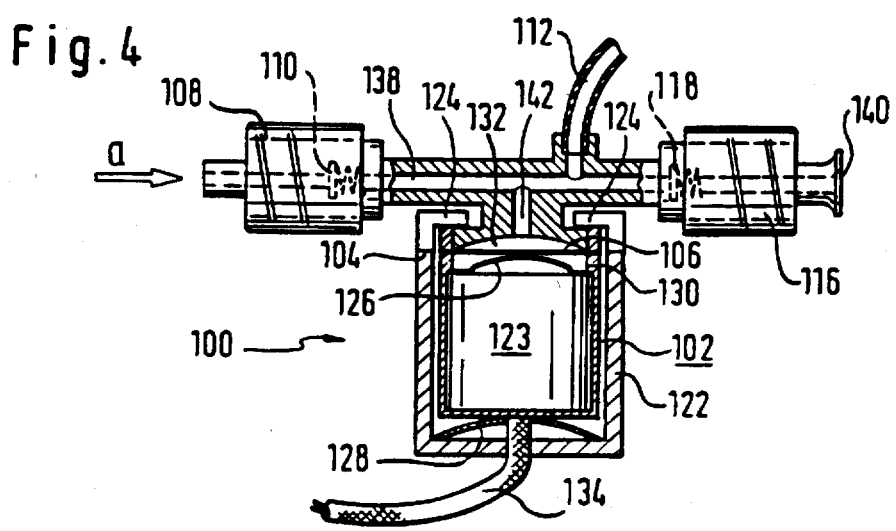
FIG. 4 represents a section taken through the embodiment in accordance with FIG. 3 of the section plane 4—4 of FIG. 3.

In FIG. 4 the arrow a indicates the direction of flow of the infusion solution. The same passes via the input Luer connector 108, the one-way valve 110 mounted here, a longitudinal duct 138 which consists of thick molded material with an extremely low degree of stretch leading to the one-way valve 118 and thence to a patient connection 140 of the Luer connector 116. From such longitudinal duct 138 there branches, as shown in FIGS. 3 and 4, a duct 142 to the above mentioned gap space 132 of the pressure transmission chamber. Furthermore a hose 112 is connected with the longitudinal duct 138 for the administration of medicaments.

Figure 5:
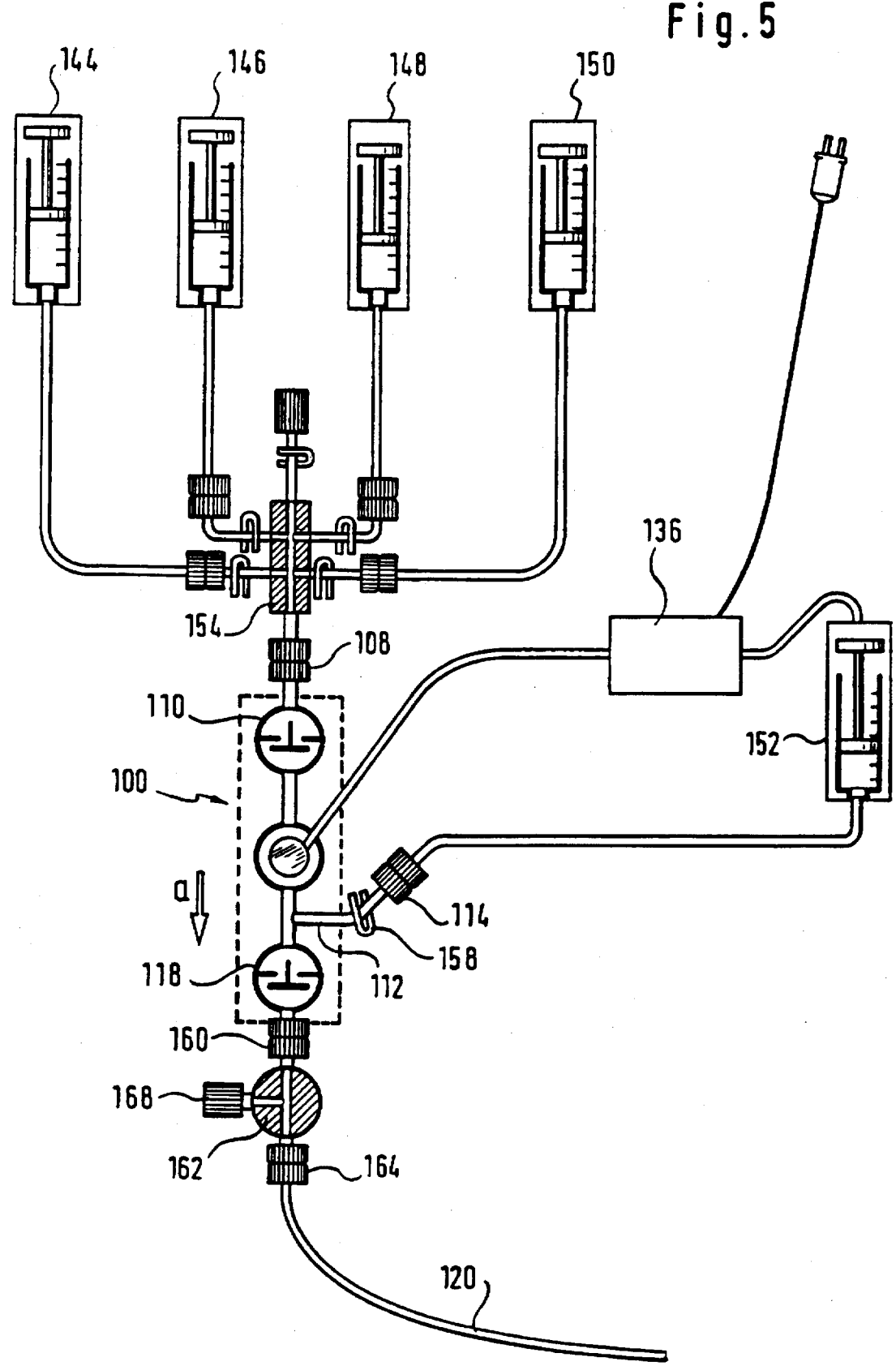
FIG. 5 diagrammatically shows the arrangement of the apparatus for infusion monitoring in accordance with the embodiment of FIG. 2 in a pump infusion system.

In FIG. 5 the reader will see an apparatus 100 for infusion monitoring in a complete infusion system with four infusion pumps 144, 46, 148 and 150 and a medicament administration pump 152 with a connected vein catheter 120.

With reference to FIG. 5 the operation of the apparatus, represented in FIGS. 2 through 4 in detail, for infusion monitoring will be explained. The apparatus 100, which is employed for sterile use once only, is filled with infusion solution via the Luer connector 108 with a built-in one-way valve 110 and a quadruple manifold 154, with which the infusion injection pumps 144, 146, 148 and 150 are connected. In this respect the pressure transmission capsule 102 with its diaphragm 106 is held down and for example squeezed with the thumb until the entire apparatus has been filled free of bubbles. Then using a hose clamp 158 the medicament administration hose 112 is closed. It is at this point that the apparatus is connected via the Luer connector 116 with the built-in one-way valve 118 with a Luer connector 160 of a three-way cock 162. The three-way cock 162 is connected via a Luer connector 164 with a vein catheter 120, which is placed in a vein sinus of the patient.

The pressure transmission capsule 102 is now inserted into the holder 124 of the housing 122, as shown in FIG. 3. By means of the spring 128 the electronic pressure sensor 123 has its rim 130 thrust firmly on the 104 of the pressure transmission capsule 102. Accordingly there will be an intimate contact between the pressure sensor diaphragm 126 and the diaphragm 106 of the pressure transmission capsule, the latter being caused to bulge. Accordingly a narrow, liquid-filled gap space is formed, which together with the longitudinal duct 138 between the one-way valves 110 and 118 only constitutes a very small liquid space only able to be compressed to an extremely slight extent. More particularly, the one-way valve 110 eliminates the compliance of the preceding, expanded infusion system, as it is illustrated in FIG. 5 for example.

The liquid space made available is sufficient for pressure measurement, and more especially the electronic pressure sensor for registration of pressure only involves an extremely small volume displacement. Accordingly a rapid recognition of infusion arrest is possible. The system is highly sensitive and reacts rapidly to changes in pressure. Even in the case of very low infusion rates reliable measurement is possible, more especially since the electronic pressure sensor utilized supplies a linear electric signal which over a large pressure range is not affected by the ambient temperature and is only proportional to the pressure.

Consequently the monitor 136 connected with the system not only indicates the pressures measured exactly, but furthermore may be set for tight warning limits for pressure monitoring.

If, as in the apparatus described, as the input one-way valve 110 a valve is employed, which is acted upon by a loading pressure (in a range of approximately 50 to 250 mbar and preferably 50 to 200 mbar) and has a set leakage rate of 5–15 µl/min and preferably 5–10 µl/min and a return flow volume rate of 0–5 μl/min and as an output one-way valve 118 a valve is employed, which is acted upon by a loading pressure of approximately 5 to 25 mbar and preferably 5 to 20 mbar and has a set leakage rate of 0–20 μl/min and preferably 0–10 μl/min and a return flow volume rate of 0–5 μl/min, then it is possible to detect arrest of infusion even at minimum infusion rates of for example 0.2–0.5 ml/h (approximately 3–8 μl/min) without 1 to 3 minutes, if such minimum quantities are infused via the medicament administration hose 112. Consequently same pass at a rate of 5 μl/min, supplemented to at least 5–10 μl/min leakage rate via the valve 110 to 10–15 μl/min, directly into the small liquid space, with an extremely low degree of compressibility, and comprising the longitudinal duct 138, the duct 142 and the gap space 132. When infusion is arrested they lead to a reduction in the alarm time to approximately ⅓ minute unlike the 3 to 9 minutes otherwise necessary and which is clinically not acceptable.

This possibility of universal application, high patient safety and freedom from disorders to be found with the infusion pressure monitoring apparatus is achieved by the following design features:
1. Arrangement adjacent to the patient,
2. the use of a one-way valve 110 with a loading pressure.
3. a very small liquid space for the transmission of pressure with a very low degree of compliance,
4. an electronic pressure sensor,
5. the supply of small infusion quantities per unit time directly into the liquid space for pressure transmission and
6. separation of such space from the patient by the one-way valve 118.

Furthermore in an alarm situation (arrest Of infusion) the electrical power supply for the medicament administration pump 152 is switched via the monitor 136. If required the other pumps 144, 146, 148 and 150 are switched off. The gage pressure still in existence owing to the one-way valves 110 and 118 in the liquid space for pressure transmission may be additionally employed in order to avoid any otherwise dangerous medicament bolus infusion. For this purpose the medicament hose connections 114 and 116 must be opened for a short time. The highly effective medicament solution will-then escape to the outside, with a decrease in pressure, from such liquid space for pressure transmission and a bolus infusion is avoided when the injection pump 152 is re-started. Owing to the three-way cock 162 placed between the outlet of the apparatus 100 and the vein catheter 120 it is possible in a very simple fashion to deal with obstruction of the catheter 120 by means of a syringe, mounted on a closed port 168, using for example physiological saline. Similarly additional administration of medicaments is possible in this manner (see FIG. 5).

Figure 6:
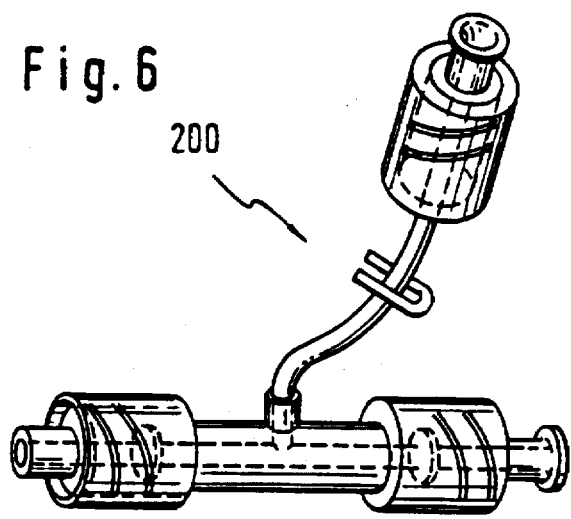
FIG. 6 shows a third embodiment of an apparatus for infusion monitoring in a perspective elevation.
Figure 7:
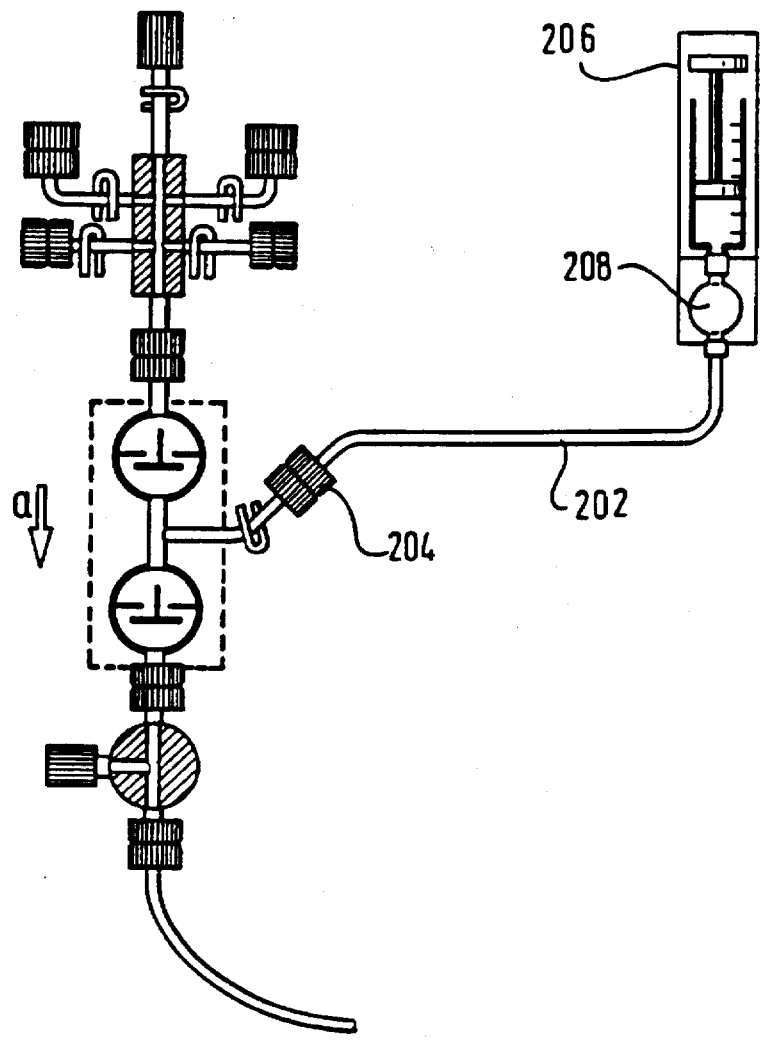
FIG. 7 diagrammatically shows the arrangement of FIG. 6 in an infusion system with injection pumps.

FIG. 6 shows a modified apparatus 200 for infusion monitoring. In FIG. 6 the apparatus 200 is substantially the same as the apparatus 100 described with reference to FIG. 4 but however with the difference that in this case the pressure transmission capsule 102 with the duct 142 is not present. The pressure transmission capsule 102 is here, as illustrated diagrammatically in FIG. 7, integrated with the thick-walled, special purpose infusion line 202 with a minimum degree of expansion, with its Luer connector 204 and arranged adjacent to an infusion syringe of a special purpose injection pump 206 by way of the electronic pressure sensor 208 thereof. By the use of a small volume pressure transmission capsule in conjunction with the low degree of compliance of the special purpose infusion line 202, the electronic pressure sensor 208, the injection pump 206 and the hydraulic transmission of pressure it is accordingly possible to achieve good results, as has been explained with reference to FIGS. 2 through 5. To the extent that no different reference numerals have been employed for the embodiments in accordance with FIGS. 6 and 7, the parts are equivalent to the parts of the embodiment of FIGS. 2 through 5.

I claim:

1. An apparatus for infusion monitoring comprising
   an infusion hose for accepting infusion flow from a single infusion flow source,
   a diaphragm,
   a pressure transmission line extending between said infusion hose and said diaphragm, said diaphragm indicating blockage in infusion flow through said infusion line from the single infusion flow source, and
   a one-way valve located in said infusion hose for placement adjacent to a patient so as to permit infusion flow only in a direction to the patient,
   said pressure transmission line including a narrow-lumen pressure transmission hose and an intermediately placed air chamber having a free end thereof connected with a pressure transmission capsule which includes said diaphragm,
   said air chamber including a piece of transparent, thick-walled hose having a wider lumen than said narrow lumen, thick walled hose of said pressure transmission line.

2. The apparatus as claimed in claim 1, wherein a second one-way valve is located in said infusion hose.

3. The apparatus as claimed in claim 2, wherein a pressure transmission capsule is connected to said diaphragm of said pressure transmission line.

4. The apparatus as claimed in claim 3, wherein said pressure transmission capsule includes an electronic pressure sensor located in a housing, said housing being secured to said diaphragm so as to place said electronic pressure sensor in contact with said diaphragm of said pressure transmission line.

5. The apparatus as claimed in claim 4, wherein said pressure transmission line includes thick-walled material with an extremely low degree of stretch and said pressure transmission capsule possesses a very small filling capacity.

6. The apparatus as claimed in claim 2, wherein said one-way valve adjacent to the patient is loaded with a pressure of 5 to 25 mbar and possesses a leakage flow rate of 0 to 20 μl/min and a return flow rate of 0 to 5 μl/min.

7. The apparatus as claimed in claim 2, wherein said second one-way valve is loaded with a pressure of 50 to 250 mbar and possesses a leakage flow rate of 5 to 15 μl/min and a return flow rate of 0 to 5 μl/min.

8. The apparatus as claimed in claim 1, wherein a T union connects said infusion hose and said pressure transmission line.

9. The apparatus as claimed in claim 8, wherein said pressure transmission line extending from said T union includes said narrow-lumen, thick-walled hose having a length between 1 and 10 cm to said air chamber.

10. The apparatus as claimed in claim 1, wherein said one-way valve is pressure loaded.

11. The apparatus as claimed in claim 1 wherein said one-way valve is integrated in a hose connector of said infusion hose.

12. The apparatus as claimed in claim 1, wherein said air chamber is dimensioned so that during routinely measured infusion pressures no infusion liquid finds its way into said pressure transmission hose.

13. The apparatus as claimed in claim 1 wherein said pressure transmission hose extending from said air chamber has length of 50 to 150 cm.

14. The apparatus as claimed in claim 1, wherein said pressure transmission line includes a connecting hose connected to said infusion line and said connecting hose having a hose clamp.

15. An apparatus for infusion monitoring comprising:

an infusion hose for accepting infusion flow from a single infusion flow source, a diaphragm, a pressure transmission line extending between said infusion hose and said diaphragm, said diaphragm indicating blockage in infusion flow through said infusion line from the single infusion flow source, a first one-way valve located in said infusion hose for placement adjacent to a patient so as to permit infusion flow only in a direction to the patient, a second one-way valve located in said infusion hose, and a pressure transmission capsule connected to said diaphragm of said pressure transmission line.

16. The apparatus as claimed in claim 15, wherein said pressure transmission capsule includes an electronic pressure sensor located in a housing, said housing being secured to diaphragm so as to place said electronic pressure sensor in contact with said diaphragm of said pressure transmission line.

17. The apparatus as claimed in claim 15, wherein said first one-way valve is loaded with a pressure of 5 to 25 mbar and possesses a leakage flow rate of 0 to 20 µl/min and a return flow rate of 0 to 5 µl/min.

18. The apparatus as claimed in claim 15, wherein said second one-way valve is loaded with a pressure of 50 to 250 mbar and possesses a leakage flow rate of 5 to 15 µl/min and a return flow rate of 0 to 5 µl/min.

19. An apparatus for infusion monitoring comprising:

an infusion hose, a pressure transmission line, a connector for connecting to an infusion device, said connector having infusion flow therethrough divided between said infusion hose and said pressure transmission line, said infusion line terminating in a one-way valve for allowing infusion flow therefrom only in a direction towards a patient, said pressure transmission line being a thick walled, minimal expansion line having two separate interconnected sections interconnected by an air chamber, said pressure transmission line terminating in a diaphragm for connection to a pressure sensitive sensor to detect infusion pressure which controls an alarm signal dependent upon infusion flow pressure.

* * * * *